US00PP14394P29

(12) United States Plant Patent
Repp

(10) Patent No.: US PP14,394 P2
(45) Date of Patent: Dec. 23, 2003

(54) COLEUS PLANT NAMED 'COPPER'

(50) Latin Name: *Coleus×hybrida*
Varietal Denomination: Copper

(76) Inventor: Ralph Repp, 423 Country Road, Waynesville, NC (US) 28785

( * ) Notice: Subject to any disclaimer, the term of this patent is extended or adjusted under 35 U.S.C. 154(b) by 0 days.

(21) Appl. No.: 10/291,072

(22) Filed: Nov. 8, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Coleus plant named 'Copper', characterized by its upright, mounded and compact plant habit; and dark rusty red and orange bi-colored leaves.

1 Drawing Sheet

Botanical classification/cultivar designation: Coleus×hybrida cultivar Copper.

BACKGROUND OF THE INVENTION

The present Invention relates to a new and distinct cultivar of Coleus plant, botanically known as *Solenostemon scutellarioides,* and hereinafter referred to by the cultivar name Copper.

The new cultivar was discovered by the Inventor in a controlled environment in Waynesville, N.C. as a seedling from a self-pollination of the *Solenostemon scutellarioides* cultivar Fack, not patented. The new Coleus was observed within the seedling progeny from the stated self-pollination in June, 2001. This seedling was selected on the basis of its unique leaf coloration.

Asexual reproduction of the new cultivar by terminal cuttings taken in Waynesville, N.C. since June, 2001, has shown that the unique features of this new Coleus are stable and reproduced true to type in successive generations.

SUMMARY OF THE INVENTION

Plants of the cultivar Copper have not been observed under all possible environmental conditions. The phenotype may vary somewhat with variations in environment such as temperature and light intensity without, however, any variance in genotype.

The following traits have been repeatedly observed and are determined to be the unique characteristics of 'Copper'. These characteristics in combination distinguish 'Copper' as a new and distinct cultivar:

1. Upright, mounded and compact plant habit.
2. Dark rusty red and orange bi-colored leaves.

Plants of the new Coleus are most similar to plants of the parent, the cultivar Fack. Plants of the new Coleus differ from plants of the cultivar Fack primarily in foliage color as plants of the cultivar Fack have dark purple, pink and green-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Coleus.

The photograph at the top of the sheet comprises a side perspective view of typical plant of 'Copper' grown in a container.

The photograph at the bottom of the sheet comprises a close-up view of typical leaves of 'Copper'.

DETAILED BOTANICAL DESCRIPTION

The cultivar Copper has not been observed under all possible environmental conditions. The phenotype may vary somewhat with variations in environment such as temperature and light intensity without, however, any variance in genotype.

The aforementioned photographs, following observations and measurements describe plants grown during the winter and spring in Encinitas, Calif., in an outdoor nursery and under conditions which approximate commercial production cultural and environmental conditions. Plants were about ten weeks from rooted cuttings and were grown in one-gallon containers. During the production of the plants, day temperatures averaged 24° C. and night temperatures averaged 19° C.

In the following description, color references are made to The Royal Horticultural Society Colour Chart, 1995 Edition, except where general terms of ordinary dictionary significance are used.

Botanical classification: *Solenostemon scutellarioides* cultivar Copper.

Parentage: Seedling from a self-pollination of the *Solenostemon scutellarioides* cultivar Fack, not patented.

Propagation:

*Type cutting.*—Terminal cuttings.

*Time to initiate roots.*—Summer: About 4 days at 21° C. Winter: About 5 to 6 days at 21° C.

*Time to develop roots.*—Summer: About 14 days at 20° C. Winter: About 14 to 17 days at 20° C.

*Root description.*—Fine, fibrous, white in color.

*Rooting habit.*—Freely branching.

Plant description:

*Form.*—Annual flowering plant; compact, upright and mounded. Moderate to rapid growth rate.

*Plant height.*—About 26 cm.

*Plant diameter.*—About 38 cm.

*Branching habit.*—Freely branching with potentially two lateral branches forming at every node.

*Lateral branches.*—Length: About 24 cm. Diameter: About 7 mm. Internode length: About 4 to 4.5 cm. Shape, in cross-section: Squarish. Texture: Pubescent. Color: 59A.

*Foliage description.*—Arrangement: Opposite; simple. Length: About 9.5 cm. Width: About 6 cm. Shape: Deltoid. Apex: Acute. Base: Attenuate to truncate. Margin: Dentate to crenate; ruffled. Texture, upper and lower surfaces: Pubescent; velvety. Venation pattern: Pinnate. Color: Young foliage, upper surface: 187B. Young foliage, lower surface: 71A. Fully expanded foliage, upper surface: Ground color, 173B, overlain with irregular areas of 179A or 185B with random touches of 146A to 146B. Fully expanded foliage, lower surface: Random and irregular areas of 187B and 179A. Venation, upper surface: 185A to 185B. Venation, lower surface: 145B to 145C. Petiole length: About 2.8 to 3.8 mm. Petiole diameter: About 2.5 mm. Petiole color: 183D.

Flower description: Flower development has not been observed.

Disease/pest resistance: Plants of the new Coleus have not been noted to be resistant to pathogens or pests common to Coleus.

Temperature tolerance: Plants of the new Coleus have been observed to tolerate temperatures from 2 to 35° C.

It is claimed:

1. A new and distinct cultivar of Coleus plant named 'Copper', as illustrated and described.

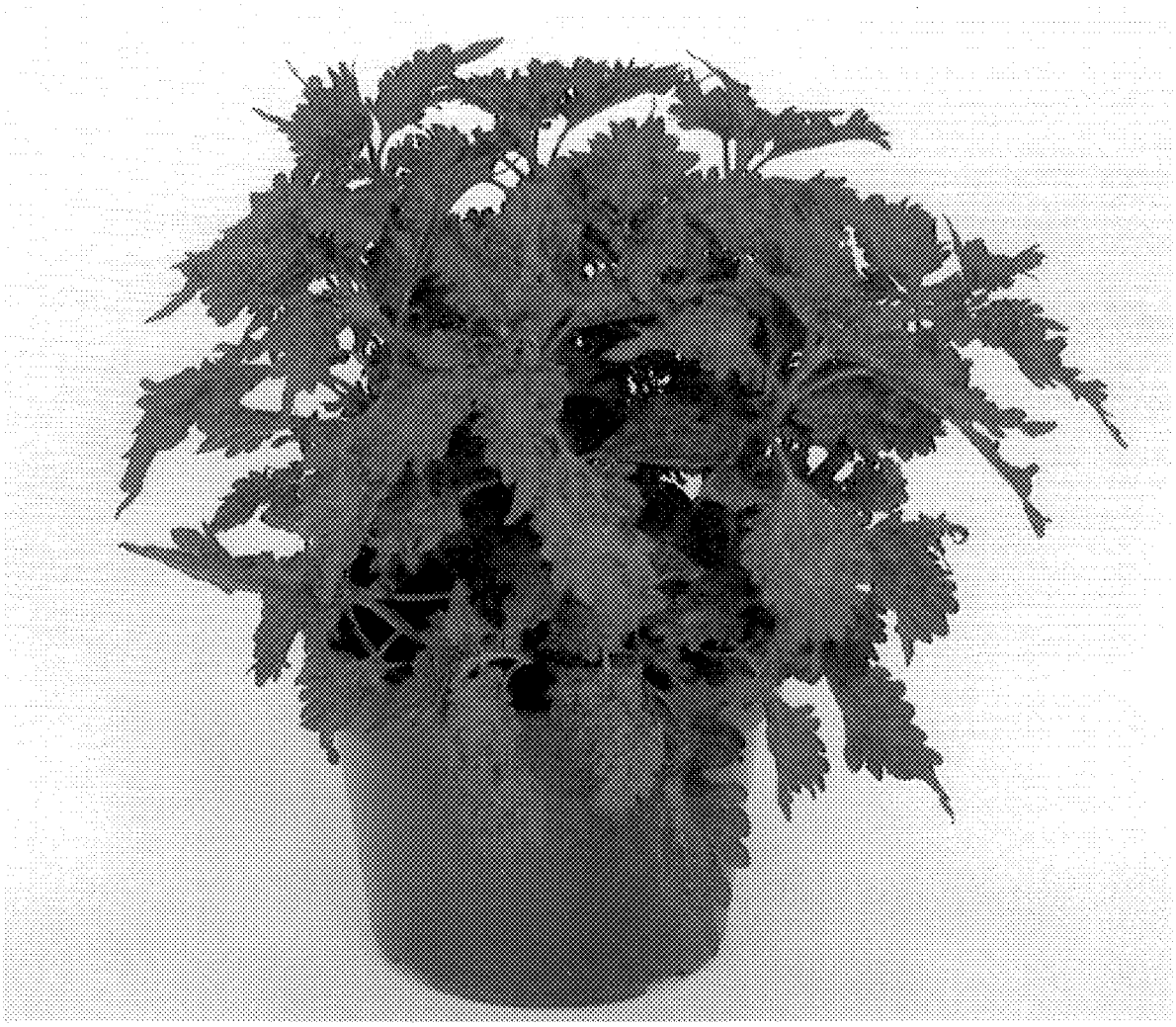
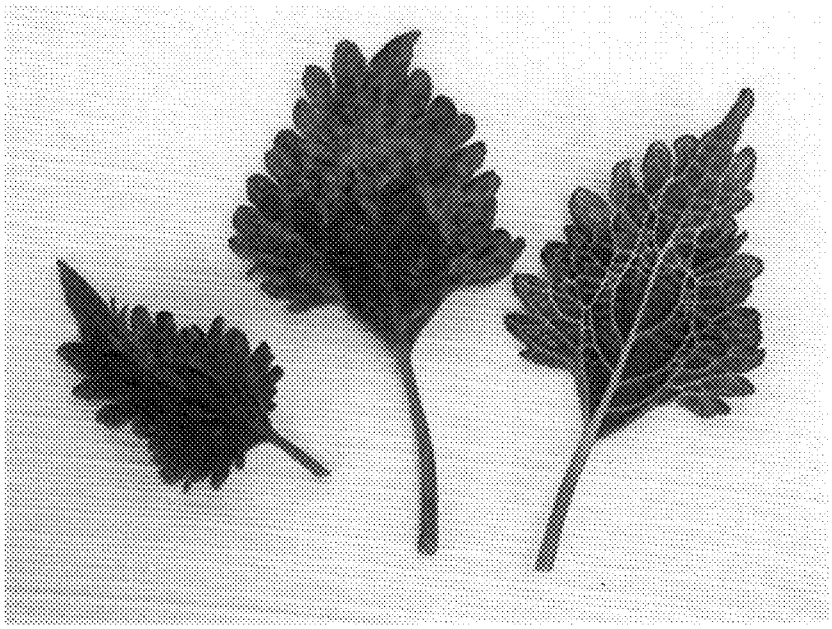

* * * * *